US006800866B2

(12) United States Patent
Amemiya et al.

(10) Patent No.: US 6,800,866 B2
(45) Date of Patent: Oct. 5, 2004

(54) ACCELERATOR SYSTEM AND MEDICAL ACCELERATOR FACILITY

(75) Inventors: Kensuke Amemiya, Hitachinaka (JP); Kazuo Hiramoto, Hitachiohta (JP); Masanobu Tanaka, Hitachi (JP); Shigemitsu Hara, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 35 days.

(21) Appl. No.: 10/101,214

(22) Filed: Mar. 20, 2002

(65) Prior Publication Data

US 2003/0048080 A1 Mar. 13, 2003

(30) Foreign Application Priority Data

Sep. 11, 2001 (JP) ....................................... 2001-275106

(51) Int. Cl.[7] ............................ A61N 5/00; H05H 9/00; H05H 13/04

(52) U.S. Cl. ................................ 250/505.1; 250/492.1; 250/396 R; 250/398; 315/502; 315/503; 315/505

(58) Field of Search ........................... 250/505.1, 492.1, 250/396 R, 398; 315/502, 503, 505

(56) References Cited

U.S. PATENT DOCUMENTS 5,363,008 A * 11/1994 Hiramoto et al. ............. 313/62
5,504,341 A * 4/1996 Glavish ................. 250/492.21
6,194,734 B1 * 2/2001 Loomis et al. ......... 250/492.21

FOREIGN PATENT DOCUMENTS

| | | | |
|---|---|---|---|
| EP | 0779081 | A2 | 6/1997 |
| EP | 0826394 | A2 | 3/1998 |
| EP | 0994638 | A1 | 4/2000 |
| EP | 1073318 | A2 | 1/2001 |
| EP | 1085786 | A2 | 3/2001 |
| JP | 7-169594 | | 7/1995 |
| JP | 2596292 | | 1/1997 |
| JP | 9-245995 | | 9/1997 |
| JP | 10-247600 | | 9/1998 |

* cited by examiner

*Primary Examiner*—Nikita Wells
(74) *Attorney, Agent, or Firm*—Crowell & Moring LLP

(57) ABSTRACT

To provide an accelerator system having a wide ion beam current control range, being capable of operating with low power consumption and a long maintenance interval and being capable of preventing unnecessarily large dose of the ion beam for irradiation from erroneously being supplied to the downstream side of the system.

In an accelerator system designed to treat the patient with irradiation of a high-energy ion beam accelerated by a post-accelerator 4 comprising a synchrotron in irradiation rooms 6 to 8, a value of ion beam current to be supplied to the post-accelerator 4 is controlled by a pre-accelerator comprising an ion source 10, quadrupole electromagnet 15, radio frequency quadrupole accelerator 17 and a drift tube type accelerator 19.

The accelerator system featuring low power consumption, a long maintenance interval and high reliability can be made available.

10 Claims, 5 Drawing Sheets

ACCELERATOR SYSTEM AND MEDICAL ACCELERATOR FACILITY

BACKGROUND OF THE INVENTION

The present invention relates to an accelerator system for irradiation with ion beams, and particularly to an accelerator system suitable for a medical application.

Recently, what is called the radiotherapy characterized by irradiating the affected part such as the part affected by cancer with the ion beam has come to attract the attention of the people. In the radiotherapy, it is necessary for the dose of the ion beam for irradiating an affected part to be controlled stably over a wide control range and over a long period time, and, in order to meet these requirements, an accelerating system such as one shown in FIG. 5 has been used conventionally.

The accelerator system shown in FIG. 5 is disclosed in the specification of Japanese Patent No. 2596292 and is designed such that an ion beam B generated at a pre-accelerator 1 including an ion source is deflected by receivers 2, 3 to be transmitted to a post-accelerator 4, where the ion beam is accelerated to acquire a necessary magnitude of energy, and is transmitted, by an emitted beam transmission system 5, to various irradiation rooms (or treatment rooms) 6, 7 and 8 for use in treatment.

When, for instance, a proton beam is used as the ion beam, necessary energy is about 250 MeV, while necessary average current is about 10 nA. Therefore, an apparatus comprising an ion source and a linear accelerator, which are arranged linearly as disclosed in the Japanese Patent Laid-Open No. 10-247600, is usually used as a pre-accelerator 1 where the ion beam B is accelerated to about 10 MeV, while a synchrotron, for instance, is used as the post-accelerator 4.

In this case, for the ion source, a hot-cathode duoplasmatron type ion source or PIG type ion source is used in general, because these ion sources are compact and simple in construction.

Incidentally, the accelerator system according to the prior art shown in FIG. 5 employs a method in which a filter 9 is inserted in an ion beam route on the downstream side of the pre-accelerator to restrict the transmission rate of the ion beam, thereby controlling the ion beam current to be introduced into the treatment rooms 6, 7 and 8.

A metal mesh, a porous plate or the like is used as the filter 9 herein. The metal mesh controls the ion beam level by varying a distance between metal wires and the number of the metal wires, while the porous plate controls the ion beam rate by varying the diameter and the number of apertures.

The above-mentioned prior art has no consideration in that a mount of the ion beam accelerated by the pre-accelerator including the ion source and the linear accelerator is always kept at its maximum throughout the period of irradiation. Thus, problems arise of a low power consumption, the shortening of maintenance intervals, and the prevention of ion beam irradiation with excessive intensity.

More particularly, in the prior art, as explained referring to FIG. 5, a filter 20 is provided in the ion beam route on the downstream side of the pre-accelerator 1 to control the level of the ion beam current. Thus, it is always necessary to keep the ion beam current at its highest level so as to meet the requirement in the treatment room 12 during the irradiation period.

Hence, in the prior art, not only the ion beam current efficiency or the power efficiency is relatively low but also the service life of the equipment becomes relatively short. In consequence, if some faults arise in the filter 20, the beam carrying a large current, without being controlled, will be sent freely to the downstream side. In the prior art, if some faults arise in the filter 20, it is safe for patient by beam current interlock. But it is not good for synchrotron operation.

As a result, the prior art has problems such as not being suitable for the saving of the power consumption, requiring the maintenance at relatively short intervals, and having difficulty in preventing the irradiation with the ion beam of an excessive intensity.

SUMMARY OF THE INVENTION

An object of the present invention is to provide an accelerator system having a wide ion beam current control range, suiting a power saving operation, capable of operating at relatively long maintenance intervals and capable of preventing an excessive dose of irradiation from being erroneously transported to the downstream side.

Another object of the present invention is to provide a medical accelerator facility having a wide ion beam control range, suiting a power saving operation, capable of operating at relatively long maintenance intervals and capable of preventing an excessive dose of irradiation from being erroneously transmitted to the downstream side.

In order to attain the above-mentioned objects, the accelerator system is configured to irradiate a target in an irradiation room with an ion beam, which is supplied from a pre-accelerator including an ion source and accelerated by a post-accelerator, and control a value of ion beam current to be applied for the irradiation of the target in the irradiation room by the pre-accelerator.

The above-mentioned objects of the present invention can also be attained by constituting the ion source with at least one of a radio frequency discharge type ion source or a microwave discharge type ion source, or by providing the pre-accelerator with a beam focusing system so that the ion beam current value can be controlled by controlling a focusing rate of the beam focusing system, or by having the pre-accelerator being at least one of a radio frequency linear accelerator or a high-frequency quadrupole accelerator or a drift tube type accelerator so that the ion beam current value can be controlled by controlling at least one of these accelerators or by controlling at least one of the two accelerators provided in combination.

Further, the above-mentioned objects can also be attained by providing the post-accelerator comprising a synchrotron or a cyclotron or a combination of the synchrotron and the cyclotron, or by providing a constitution of enabling the ion beam current value to be controlled according to a predetermined treatment procedure for treatment in the irradiation room, or by using an ion beam being a proton beam.

Further, the above-mentioned objects can also be attained by providing the accelerator system according to any one of the claims 1 through 7 as an accelerator for medical application.

BRIEF DESCRIPTION OF THE DRAWINGS

The above and other objects, features and advantages of the present invention will become more apparent from the following description taken in connection with the accompanying drawings, in which.

DETAILED DESCRIPTION OF THE PREFERRED EMBODIMENTS

An accelerator system and a medical accelerator facility according to an embodiment of the present invention will be described with reference to the drawings below.

Figure 5:
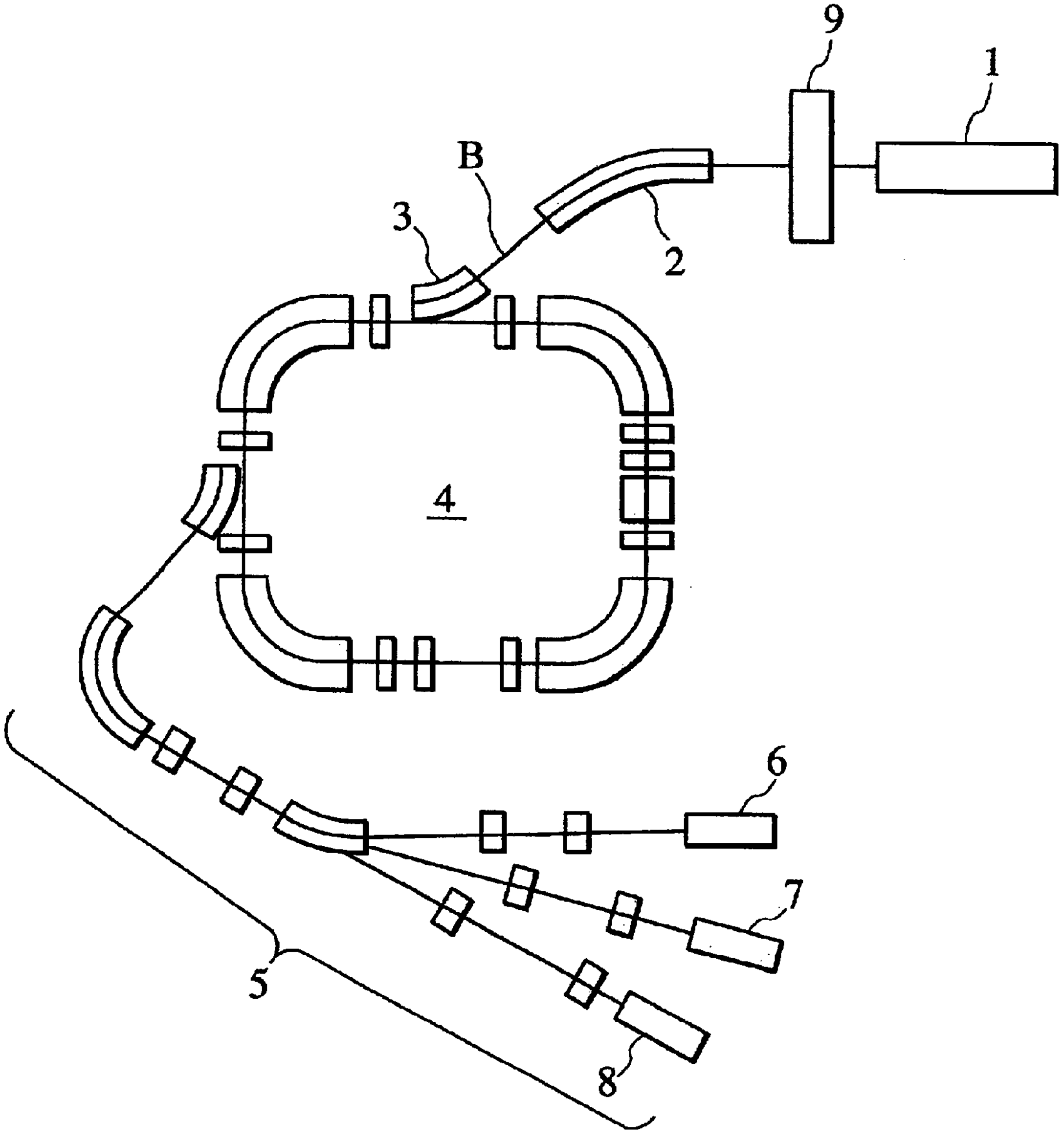
FIG. 5 is a constitutional diagram of an accelerator system according to the prior art.

In the first place, an accelerator system according to an embodiment of the present invention will be described referring to FIG. 1. In this embodiment, a post-accelerator 4 comprising a cyclotron, an outputted beam transmission system 5 and irradiation rooms (radiotherapy rooms) 6, 7 and 8 are identical to those used in the prior art as is illustrated in FIG. 5.

Figure 1:
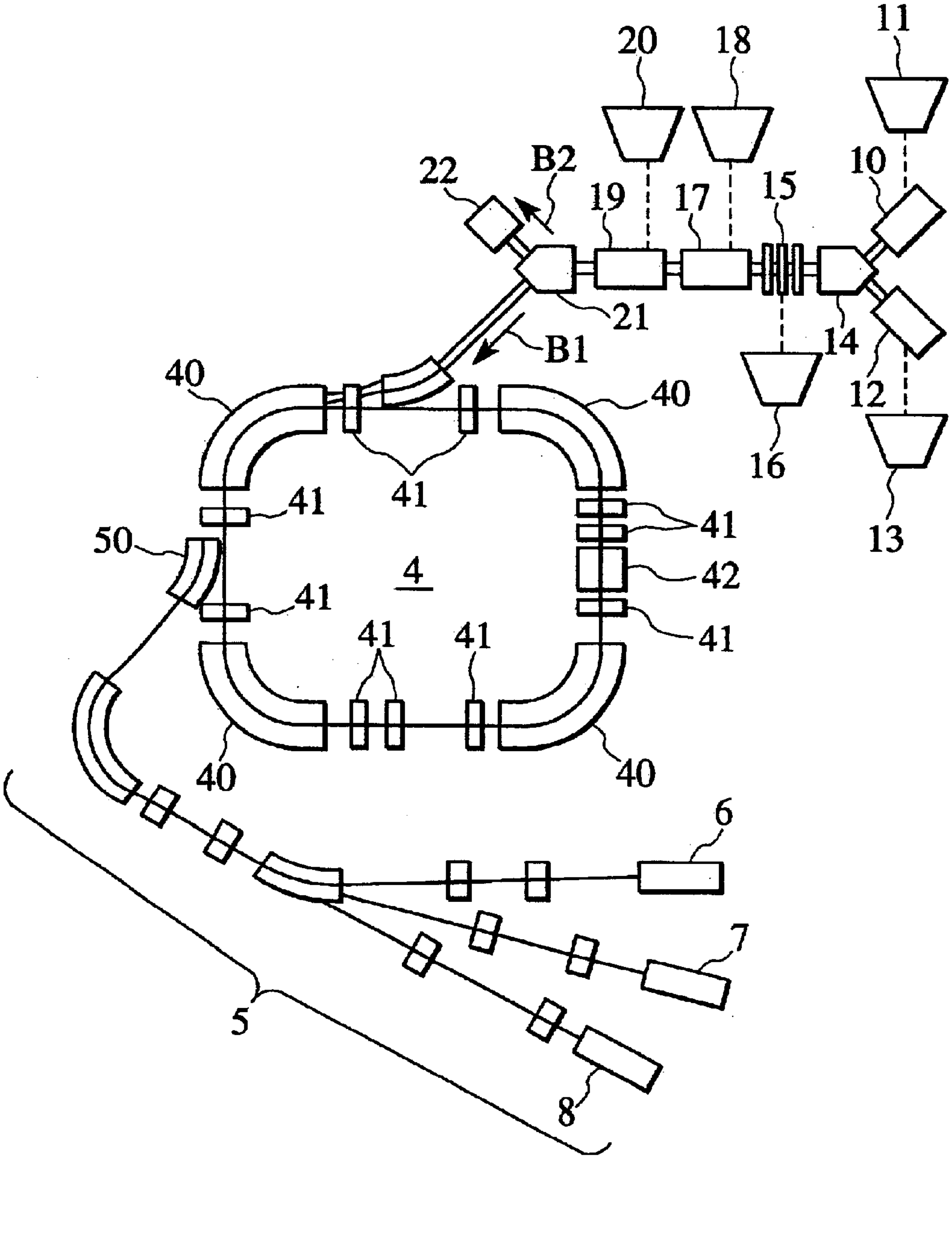
FIG. 1 is a constitutional diagram of an accelerator system according to an embodiment of the present invention.

In the embodiment shown in FIG. 1, reference numeral 10 represents a microwave discharge type ion source; 11, an ion source current controller; 12, a radio frequency discharge type ion source; 13, an ion source current controller; 14, a deflecting electromagnet; 15, a quadrupole electromagnet; 16, a quadrupole electromagnet controller; 17, a radio frequency quadrupole accelerator; 18, a radio frequency quadrupole accelerator controller; 19, a drift tube type accelerator; 20, a drift tube type accelerator controller; 21, a branch deflecting electromagnet; 22, an irradiator.

The microwave discharge type ion source 10 is used as a main ion source for generating a long-lasting high current beam. The radio frequency discharge type ion source 12 is used as a stand-by ion source and switched by the deflecting electromagnet 14.

The microwave discharge type ion source may be substituted for the radio frequency discharge type ion source, or a single ion source without any stand-by ion source may be used.

The reason why the microwave discharge type ion source or the radio frequency discharge type ion source is used is that these ion sources not only can provide a high positive (+) ion beam current but also have long lives.

In particular, in the case of the microwave discharge type ion source, when the whistler mode, which enables the microwave to be propagated in a magnetic field whose intensity is higher than that of the electron cyclotron resonance magnetic filed, is applied, a high density plasma can be produced to maximize the output of the ion source, and thus a wide beam current control range can be set for the final beam irradiation stage, thereby enabling the ion beam to be produced at a high voltage such as about 50 kV, regardless of the kind of the ion source.

The quadrupole electromagnet 15 comprises three stages and constitutes a magnetic lens system, namely, a focusing lens system designed for focusing the beam to be outputted to the pre-accelerator. In this embodiment, the quadrupole electromagnet 15 is used, but the same effect can be obtained by using an einzel lens, solenoid lens and quadrupole electric field.

The magnetic lens system is designed to focus the beam for enabling it to strike a small area, about 10 mm in diameter, of the high-frequency linear accelerator (to be described in detail later); in this case, the solenoid lens is capable of temporarily focusing the beam by means of a weak magnetic force, while the quadrupole lens is capable of producing a large focusing force in radial directions to focus the beam to a higher degree.

The radio frequency quadrupole accelerator 17 and the drift tube type accelerator 19, when used in combination, function as a radio frequency linear accelerator capable of generating a high-energy beam of about 10 MeV.

In this embodiment, the radio frequency quadrupole accelerator 17 is a linear accelerator designed for the acceleration in a relatively low-intensity energy range and is capable of producing a beam current of higher value, compared with the electrostatic accelerator having an acceleration performance equivalent to that of the former. Next, the drift tube type accelerator 19 is a linear accelerator designed for use in a relatively high-energy range such as 3–10 MeV and is capable of providing a high beam current.

Further, in this embodiment, a multi-pole (comprising even number of magnetic poles such as six magnetic poles or more) type radio frequency accelerator may be substituted for the radio frequency quadrupole accelerator, and also the radio frequency accelerator other than these radio frequency accelerators may be used.

The components described in the foregoing constitute the pre-accelerator. The ion beam accelerated to about 10 MeV by the pre-accelerator is deflected by the branch deflecting electromagnet 21. When a high energy is necessary, in order to generate the beam for the treatment of a patient, the ion beam is switched to an ion beam B1 to be inputted to the post-accelerator 4, while when using a low-energy beam, the ion beam is switched to an ion beam B2 to be inputted to the irradiator 22.

The post-accelerator 4 comprises a known synchrotron and is designed so that the ion beam inputted thereto at an energy intensity of about 10 MeV is made to circuit along a predetermined circuit route by means of a deflecting electromagnet 40 and various focusing systems 41 and so that the ion beam is accelerated progressively in a high-frequency acceleration cavity 42 as the number of times of the circuiting increases until the energy intensity finally reaches the level of about 200–250 MeV before being outputted to the beam transmission system 5.

The outputted beam transmission system 5 efficiently transmits the high-energy ion beam, which has been transmitted from the post-accelerator 4 and received by the branch deflecting electromagnet 50, into a plurality of irradiation rooms 6 through 8.

In each of the irradiation rooms 6, 7 and 8, the patient is treated with the irradiation of the ion beam. In applying the treatment, it is necessary for the intensity of the beam current for irradiation to be varied depending on the shape of the affected part and the progress of the condition of the affected part. Thus, in order to meet this requirement, the irradiation program is prepared in advance so that the irradiation with the ion beam can be made accordingly. The present invention is characterized in that the beam current is controlled on the side of the pre-accelerator prior to the input of the ion beam to the post-accelerator 4.

In the case of the embodiment of the present invention, the method of controlling the ion beam is broadly divided into the following three methods.

(1) A method of controlling the ion beam by the ion source.

(2) A method of controlling the ion beam by the focusing lens.

(3) A method of controlling the ion beam by the radio frequency accelerator.

The above control methods will be described one by one in the following.

Figure 2:
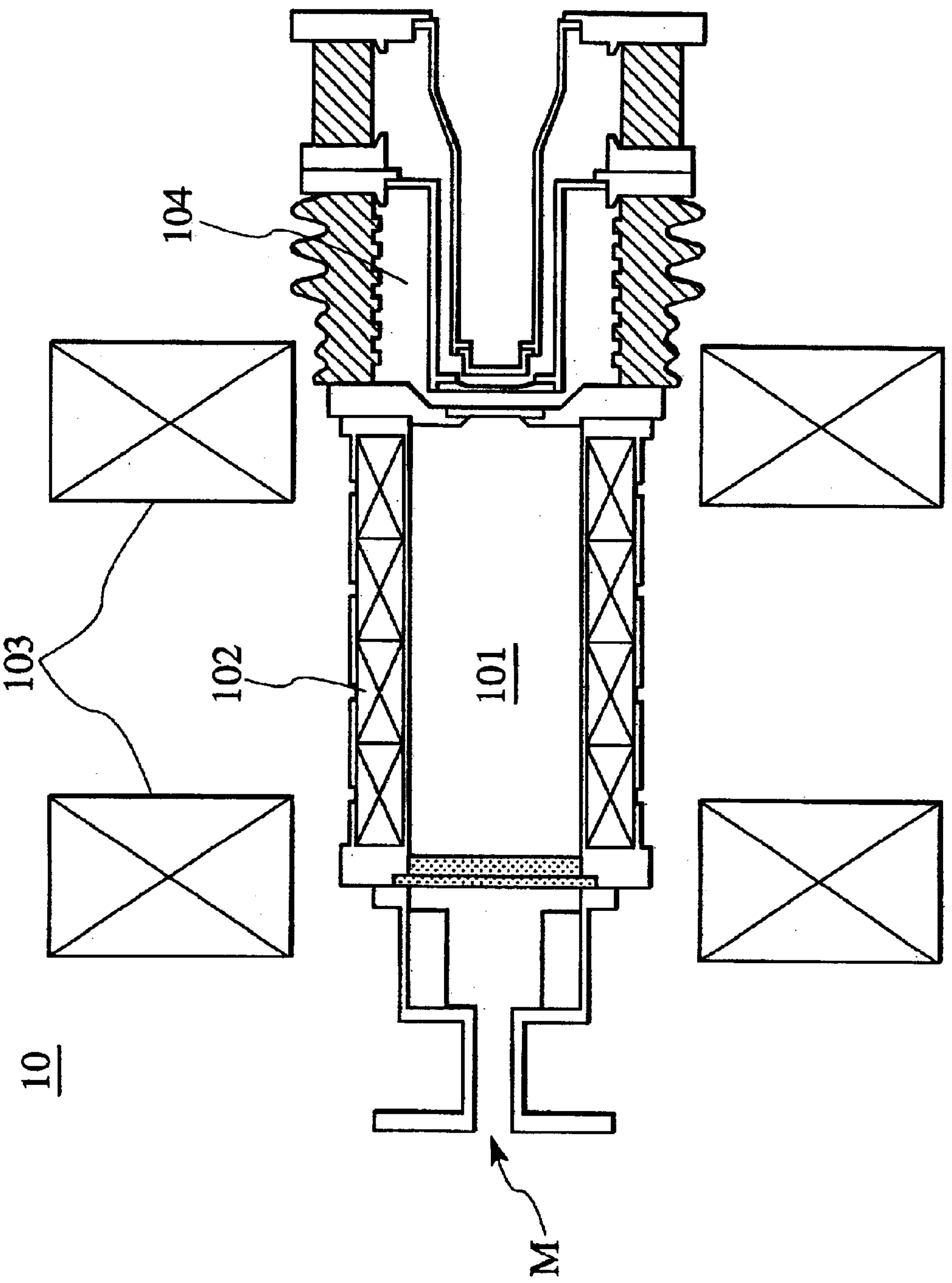
FIG. 2 is a constitutional diagram showing an example of a microwave discharge type ion source according to the embodiment of the present invention.

First, (1) the method of controlling the ion beam by the ion source will be described referring to FIG. 2. FIG. 2 shows the microwave discharge type ion source 10 according to an embodiment of the present invention, wherein a substantially cylindrical discharge room 101 to which microwaves M are supplied from an opening shown on the left-hand side in the figure, while an extraction electrode 104, comprising three pieces of stainless steel, copper and molybdenum materials, is provided on the right-hand side.

Permanent magnets 102 are provided along the outer circumference of the discharge room 101, and further, solenoid coils 103 are also provided, thereby forming their magnetic fields. The interaction between the magnetic fields caused by the permanent magnets and solenoid coils and the microwaves M generates high-density plasma in the discharge room 101, and the induction electrode 104 induces the ion beam from the generated high-density plasma to function as an ion source.

For the case of the microwave discharge type ion source 10, a voltage for inducing the ion beam is normally about 50 kV, and the value of the ion beam current can be controlled by using some parameters. For instance, the value of the ion beam current can also be controlled by using, as a parameter, the power of the microwaves M to be supplied to the discharge room 101. In addition, the value of the ion beam current can be controlled by changing, as a parameter, the intensity of the magnetic field created by the solenoid coils 103.

Further, the ion beam current value can also be controlled by varying, as a parameter, the induction voltage applied to the extraction electrode 104. Further, the ion beam current can also be controlled by adjusting, as a parameter, a gas pressure in the discharge room 101. Needless to say, the ion beam current can also be controlled by the combination of these parameters.

First, when using the microwave power as a parameter, the ion beam intensity is varied by controlling the anode current of the magnetron of the microwave oscillator (not shown) so that the microwave output and the ion beam intensity can be varied.

Next, when using the intensity of the magnetic field as a parameter, the value of the current supplied to the solenoid coil 103 is varied to bring about a variation in the plasma density and the resulting variation in the ion beam intensity.

Furthermore, when using the induced voltage as a parameter, the output voltage of the high voltage power source that applies the induction voltage to the extraction electrode 104 may be controlled. In addition, when using the gas pressure as a parameter, the gas pressure-regulating valve may be controlled to adjust the supply pressure of the gas for plasma. These two factors can easily be used as the parameters.

Thus, in this embodiment, the ion power source current controller 11 is provided with these parameter control functions, namely, the microwave power control function, coil current control function, induction voltage control function and gas pressure control function, thereby enabling the value of the ion beam current specified for the target (the affected part) in each of the irradiation rooms 6, 7, 8 to be referred so that each of the parameters can be controlled by having the value of the ion beam current conform to the ion beam current value specified by the beam irradiation program of each patient concerned.

In this embodiment, such control of the ion beam within the normal control range, for instance, is made mainly by controlling the microwave power and the coil current, but, when the control of the ion beam is required to cover a wider range, the control by the induced voltage and the control by the gas pressure are also used in combination with other control methods.

In this embodiment, the reason why the control of the ion beam by the microwave power and that by the coil current are primarily used is that these control methods are good in response and will not affect the route of the ion beam.

Further, in this embodiment, various combinations of the parameters, namely, the combinations of four different parameters, combination of two different parameters, combination of two different combinations, combination of three different parameters, combination of four different combinations or the like, are possible, thereby readily enabling the ion beam to be controlled over a wide range, 10–100 times the control range available by the prior art.

Next, (2) the method for controlling the ion beam by the focusing lens will be described. The ion beam can readily be controlled by the current control function provided in the quadrupole magnet 15 incorporated into the quadrupole electromagnet controller 16. More specifically, the degree of focusing of the inputted ion beam can be controlled by controlling the current value of the quadrupole electromagnet 15, whereby the value of the beam current to be inputted to the radio frequency linear accelerator in the following stage can be varied.

In this embodiment, controlling the current in the quadrupole electromagnet 15 causes the route of the ion beam to be altered. In this case, if optimal focusing conditions have been set for the ion beam before the route of the ion beam was altered, controlling the current in the quadrupole electromagnet 15 will cause the previously set focusing conditions to be offset from the optimal conditions, and the focusing will be adjusted as a result. On the other hand, in the radio frequency linear accelerator at the following stage, since the focusing conditions for the incoming beam have been set strictly, the change in the focusing conditions will result in the change in the beam current value.

Lastly, (3) the method for controlling the ion beam current by the radio frequency linear accelerator will be described. This accelerator comprises the radio frequency quadrupole accelerator 17 and the drift tube type accelerator 19. First, the control by using the radio frequency quadrupole accelerator 17 will be described referring to FIG. 3.

Figure 3:
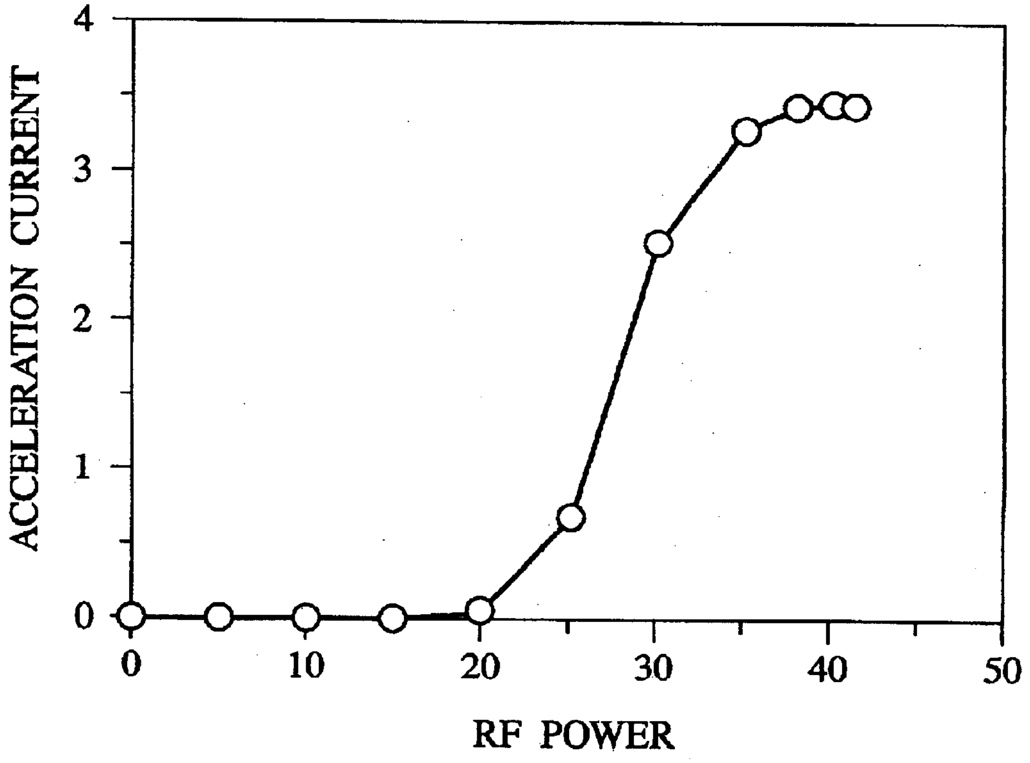
FIG. 3 is a diagram showing acceleration characteristics of a radio frequency quadrupole accelerator.

FIG. 3 is a diagram showing the characteristics of variations in the accelerating current relative to the RF power supplied to the radio frequency linear accelerator. This diagram indicates that the accelerating current starts to increase when the RF power exceeds a certain level, and the accelerating current will be saturated beyond a certain range regardless of the increase in the RF power, thereby also indicating that the accelerating current (ion beam current) can be controlled over a considerably wide range by controlling the RF power over a certain range.

Thus, the value of the beam current to be inputted to the post-accelerator can readily be controlled by incorporating the function of controlling the RF power to be supplied to the radio frequency quadrupole accelerator 17 by the radio frequency quadrupole accelerator controller 18.

This also applies to the case of the drift tube type accelerator 19. For instance, the value of the ion beam current can also be controlled by providing the drift tube type accelerator controller 20. This means that the control of the beam current value over a wider range can be made possible by using these accelerators in combination.

In the foregoing, while three different ion beam current control methods, namely (1) the control method by the ion source, (2) the control method by the focusing lens and (3) the control method by the radio frequency accelerator have been discussed separately, according to the embodiment of the present invention, these methods may be combined, e.g., either as the combination of any two control methods or as the combination of all the three control methods. The combined use of these methods enables the ion beam current to be controlled over a wider range.

Thus, as compared with the prior art in which the filter such as the metal mesh is used in controlling the ion beam current value, the above-mentioned embodiment of the present invention not only enables the operating power of the ion source to be reduced to the lowest possible level for power saving operation but also enables the burden on the ion source to be reduced during the operation by using a low beam current for irradiation, thereby contributing to the extension of the maintenance interval, an increase in the operation time and the resulting improvement in the operation rate.

Further, according to the present embodiment, for the operation using a low ion beam current for irradiation, the ion beam current can be reduced to a low level at the prior stages such as the stages of the ion source, focusing lens system, radio frequency linear accelerator or the like, and, as a result, a higher reliability of the operation can be obtained compared with the prior art using the filter of the metal mesh and the like, as described in the following.

In the case of the prior art using the filter such as the metal mesh for controlling the ion beam current, the value of the ion beam current is set to a maximum value at the prior stage of the system, so that, when the filter such as the metal mesh has become wrong, the ion beam current at its maximum level may be supplied directly to the downstream stages, even to the irradiation room at worst.

Whereas in the case of the present embodiment, the ion beam current value can be reduced to a necessary level at the prior stages such as the stages of the ion source, focusing lens system, radio frequency accelerator system before being transmitted, so that the ion beam current at its maximum value will never be transmitted directly to the following stages, thereby maintaining a high reliability of the operation.

Now, in the embodiment shown in FIG. 1, the deflecting electromagnet 21 is provided on the side of the pre-accelerator so that the ion beam is directed to be inputted to the irradiator 60 for the irradiation by using a low-energy beam, while the ion beam is directed to be inputted to the post-accelerator 4, comprising the synchrotron, for the irradiation by using a high-energy beam.

According to the present embodiment, the post-accelerator 4 comprising the synchrotron generates a proton beam for a cancer therapy in the irradiation rooms 6 through 8, while the irradiator 22 is designed for preparing the radioactive agent for diagnosing the progress of the cure following the cancer therapy and for a evaluation test such as an elemental analysis.

Thus, according to the present embodiment, a single system is not only capable of carrying out the treatment of the patient but also capable of generating the ion beam for the diagnosis and preparation of the medicines for the treatment, thereby largely contributing to an improvement in the operating efficiency of the system.

In the case of the present embodiment, needless to say, it is possible to use only the high-energy generating system on the side of the synchrotron without using the branch deflecting electromagnet 21.

Further, the embodiment of the present invention illustrated in FIG. 1 provides an accelerator system, which is not only capable of operating over a wide ion beam current control range but also is capable of carrying out the diagnosis and treatment of the patients, as wall as the preparation of the medicines for treatment, thereby promising great advantages in the use thereof.

A case where the present invention is applied to a medical accelerator facility will be described referring to FIG. 4. In the figure, reference numeral 60 represents a concrete wall separating a compartment 61 containing a pre-accelerator, a compartment 62 containing a diagnosis system and medicines for treatment preparation system, a compartment 63 containing a synchrotron, and compartments 64, 65 and 66 respectively containing irradiation treatment rooms 6, 7 and 8.

Figure 4:
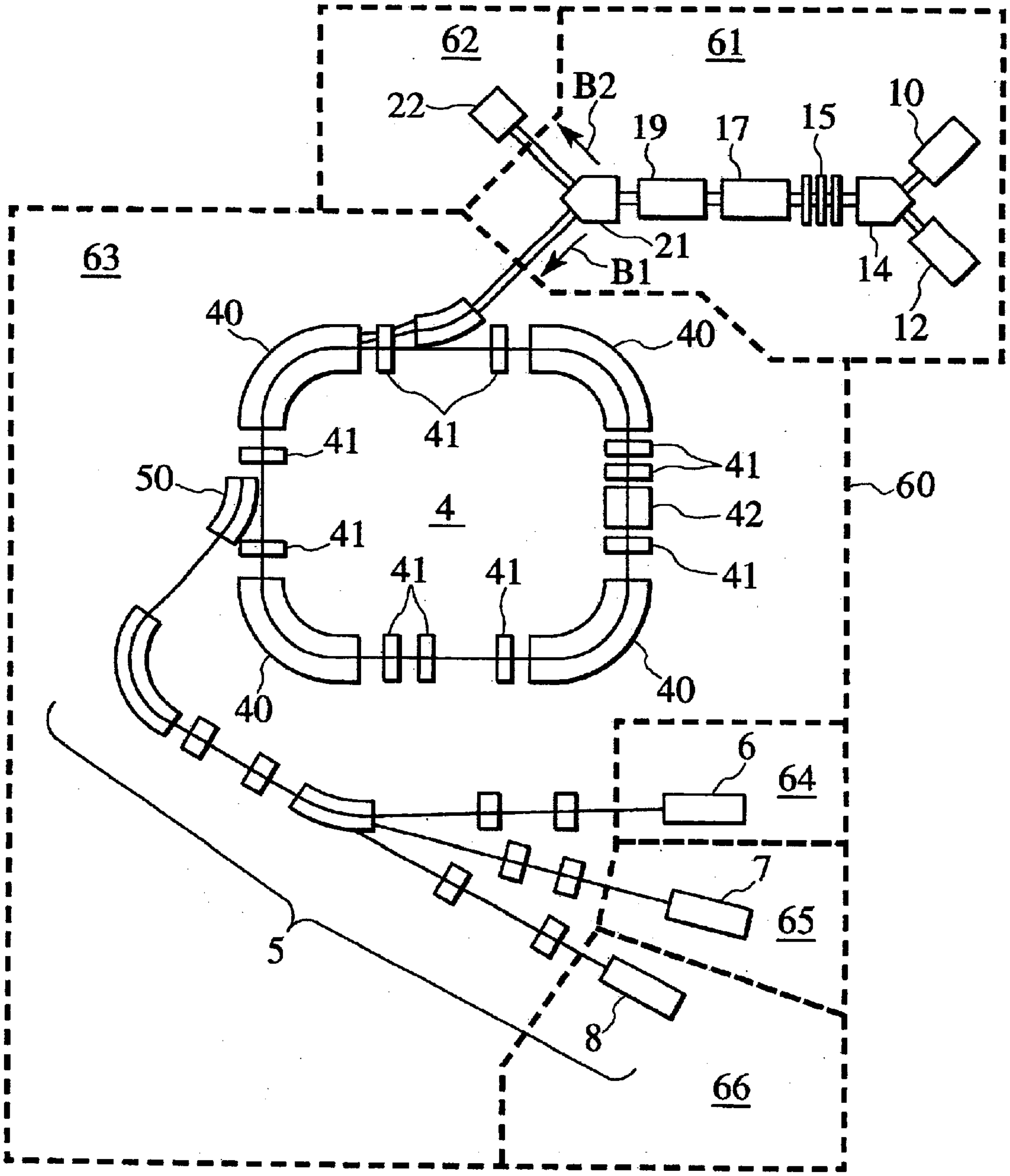
FIG. 4 is a constitutional diagram of a medical accelerator facility according to an embodiment of the present invention.

FIG. 4 shows another embodiment of the present invention wherein the various components of the medical accelerator facility as the embodiment shown in FIG. 1 are separately installed in the different compartments 61 through 66. As seen from the figure, the component comprising the pre-accelerator is installed in the compartment 61; the irradiator 22, in the compartment 62; the synchrotron constituting the post-accelerator 4, in the compartment 63; the irradiation rooms 6 through 8, in the compartments 64 through 66, respectively.

In the embodiment shown in FIG. 4, the concrete wall 60 is provided with a function of shielding the components against the ion beam such as a beam of proton so that the maintenance and inspection work for any of the compartments can be carried out irrespective of the operation of the systems in other compartments, thereby not only enabling the treatment and the diagnosis to be carried out separately but also contributing to a substantial improvement in the operating efficiency of the whole system.

Further, the above-mentioned embodiments are concerned with the case where the synchrotron is used as the post-accelerator, but the cyclotron may be substituted for the synchrotron, or both the synchrotron and the cyclotron may be used in combination. Needless to say, it is also permitted to use a plurality of post-accelerators so that the ion beam can be accelerated sequentially by these post-accelerators.

The present invention surely provides an accelerator system and medical accelerator facility featuring a wide beam current control range, low power consumption and long maintenance interval.

Furthermore, the present invention is designed so that the ion beam having unnecessarily high intensity will not be supplied to downstream stages of the system even if some troubles have occurred in the system, thereby surely providing an accelerator system and medical accelerator facility with high reliability.

Although the invention has been described in its preferred embodiments with a certain degree of particularity, obviously many changes and variations are possible therein. It is therefore to be understood that the present invention may be practiced otherwise than as specifically described herein without departing from the scope and spirit thereof.

What is claimed is:

1. An accelerator system, comprising: a pre-accelerator including an ion source comprising at least one of a radio frequency discharge-type ion source and a microwave discharge-type ion source;

a post-accelerator for accelerating an ion beam supplied from the pre-accelerator and transporting the ion beam to an irradiation portion for irradiating a target in an irradiation room with the ion beam; and a first control apparatus configured to control a value of current of the ion beam being supplied from the pre-accelerator to the post-accelerator by controlling said ion source.

2. The accelerator system according to claim 1, further comprising a second control apparatus;

wherein said pre-accelerator is provided with a beam focusing system, configured to control the value of the current by controlling a focusing power of the beam focusing system.

3. The accelerator system according to claim 1, further comprising a second control apparatus, configured to control a value of the current by controlling at least one of said accelerators or by controlling at least one of the two different accelerators usable in combination, wherein the pre-accelerator comprises at least one of a radio frequency linear accelerator, a radio frequency quadrupole accelerator and a drift tube type accelerator.

4. The accelerator system according to claim 1, wherein said post-accelerator comprises a synchrotron, a cyclotron, or a combination of the synchrotron and the cyclotron.

5. The accelerator system according to claim 1, wherein the value of ion beam current is controlled according to a predetermined treatment procedure for treatment in the irradiation room.

6. The accelerator system according to claim 1, wherein said ion beam is a proton beam.

7. A medical accelerator facility comprising the accelerator system according to claim 1, wherein the accelerator system is a medical accelerator for patient care.

8. An accelerator system, comprising:

a pre-accelerator including an ion source and a beam focusing system;

a post-accelerator for accelerating an ion beam supplied from the pre-accelerator and transporting the ion beam to an irradiation portion for irradiating a target in an irradiation room with the ion beam; and a first control apparatus configured to control a value of current of an ion beam supplied from the pre-accelerator to the post-accelerator by controlling a focusing power of the beam focusing system.

9. The accelerator system according to claim 8, further comprising a second control apparatus configured to control a value of the current by controlling at least one of said accelerators or by controlling at least one of the two different, accelerators which are usable in combination;

wherein the pre-accelerator comprises at least one of a radio frequency linear accelerator, a radio frequency quadrupole accelerator, a radio frequency quadrupole accelerator and a drift tube type accelerator.

10. An accelerator system, comprising:

a pre-accelerator including an ion source;

a post accelerator comprising at least one of a radio frequency linear accelerator, a radio frequency quadrupole accelerator and a drift tube type accelerator for accelerating an ion beam supplied from the pre-accelerator and transporting the ion beam to an irradiation portion for irradiating a target in an irradiation room with the ion beam; and a control apparatus configured to control a value of the current by controlling RF power supplied to at least one of said accelerators or by controlling at least one of the two different accelerators which are usable in combination.

* * * * *